United States Patent [19]

Collier et al.

[11] Patent Number: 5,130,300

[45] Date of Patent: * Jul. 14, 1992

[54] METHOD FOR ENHANCING GROWTH OF MAMMARY PARENCHYMA

[75] Inventors: Robert J. Collier, University City; Michael F. McGrath, Chesterfield, both of Mo.

[73] Assignee: Monsanto Company, St. Louis, Mo.

[*] Notice: The portion of the term of this patent subsequent to Oct. 22, 2008 has been disclaimed.

[21] Appl. No.: 493,256

[22] Filed: Mar. 14, 1990

Related U.S. Application Data

[63] Continuation-in-part of Ser. No. 92,009, Sep. 2, 1987, Pat. No. 5,059,586, which is a continuation-in-part of Ser. No. 837,477, Mar. 7, 1986, abandoned.

[30] Foreign Application Priority Data

Feb. 19, 1987 [CA] Canada ................... 530136

[51] Int. Cl.⁵ .................. A61K 37/24; A61K 37/36
[52] U.S. Cl. ........................ 514/12; 514/21; 514/2
[58] Field of Search ............ 514/2, 12, 21; 424/105

[56] References Cited

U.S. PATENT DOCUMENTS 4,742,003 5/1988 Derynck et al. ............... 435/68
4,816,561 3/1989 Todaro .......................... 530/324
4,816,561 3/1989 Todaro .......................... 530/324
5,059,586 10/1991 Collier .......................... 514/12

FOREIGN PATENT DOCUMENTS

0190018A2 6/1986 European Pat. Off. .
0014799 1/1988 Japan .

OTHER PUBLICATIONS

"α-Transforming Growth Factor Secreted by Untransformed Bovine Pituitary Cells in Culture" Samsoondar et al., J. Biological Chemistry 261:14408-14413 (1986).
Korbin, M. S. et al. (1987) Endocrinology 121: 1412-1416 "α-Transforming Growth Factor in Bovine Anterior Pituitary Gland: Secretion by Dispersed Cells and Immunohistochemical Localization".
Eisa, JP0014799, published Jan. 1988, Abstract in English.

Primary Examiner—F. T. Moezie
Attorney, Agent, or Firm—Wayne R. Eberhardt; Carol H. Clayman; George R. Beck

[57] ABSTRACT

The growth of milk-producing mammary parenchyma in a mammal can be significantly enhanced by administering to the mammal by intramammary infusion a substance having a mitogenic effect on mammary epithelial cells in said mammal. Good growth enhancement can be achieved using very small quantities of such substances, and in relatively short periods of time.

23 Claims, No Drawings

METHOD FOR ENHANCING GROWTH OF MAMMARY PARENCHYMA

CROSS-REFERENCE TO RELATED APPLICATION

This is a continuation-in-part of U.S. Pat. No. 5,059,586 which, in turn, is a continuation-in-part of application Ser. No. 837,477 filed Mar. 7, 1986, now abandoned.

BACKGROUND OF THE INVENTION

Milk production by a mammal is ultimately limited by the amount of mammary parenchyma (secretory tissue) in the mammary gland. Typically, milk yield has been found to be highly correlated with parenchyma wet weight, dry weight, dry fat-free weight and total gland DNA. In 43 Proc. N.Z. Soc. Anim. Prod. 71 (1983), Davis et al attributed increased milk production in genetically superior animals entirely to increased udder volume which is also related to the quantity of parenchyma cells.

Classical evidence indicates that mammary parenchyma growth is directed by pituitary, ovarian, adrenal, placental or locally-derived tissue factors. See Cowie, 15 Mono-graphs on Endocrinology (1980) and U.S. Pat. No. 4,521,409 issued Jun. 4, 1985 to Bauman and Sejrsen, in which it is disclosed that growth of mammary parenchyma in a ruminant can be increased by administering a growth hormone (somatotropin) into the ruminant's blood stream between about the onset of puberty and about the first parturition (preferably about the first conception).

If administered into an animal's blood stream, most mitogens for mammary parenchyma cells bind additionally to receptors in many of the animal's other tissues. Due to such dilution of the desired effect on mammary growth-stimulating receptors, increasing mammary parenchyma via administration into the blood stream would be expected to require relatively large quantities of such mitogens. Hence there is great incentive to develop a practical technique for increasing the milk production capacity and/or efficiency of a mammal that is not dependent on administration into the mammal's blood stream.

Using rabbits, mice and rats that were physiologically abnormal, i.e., ovariectomized and/or pretreated (e.g. with a reproductive hormone) to induce pseudopregnancy, studies have been made of effects on mammary gland development by subcutaneous injection of a somatotropin and/or other hormones, implants that released cholera toxin, or intraductal injection of "lactogenic hormone". Lyons et al, 50 Proc. Soc. Exper. Biol. Med. 308-11 (1942) and 14 Recent Prog. Hormone Res. 219-54 (1958); Fiddler et al, 49 J. Endocrin. 459-69 (1971); Daniel et al, 224 Sci. 1245-47 (1984); and Silberstein et al, 81 Proc. Natl. Acad. Sci. USA 4950-54 (1984). Based on other studies using rabbits that were pregnant or pretreated (e.g. with a reproductive hormone) to induce pseudopregnancy, it has been reported that intraductal injection of prolactin or "lactogenic hormone" induced lactation. Bradley et al, 14 J. Endocrin. 28-36 (1956) and Meites et al, 150 Amer. J. Physiol. 394-99 (1947). Others have studied in vitro effects of mitogens such as an epidermal growth factor, with or without insulin, on the growth of culture mammary cells of various animal species. Imagawa et al, 79 Proc. Natl. Acad. Sci. USA 4074-77 (1982); Taketani et al, 113 (3) Endocrin. 871 (1983) and 80 Proc. Natl. Acad. Sci. USA 2647-50 (1983); Tonelli et al, 285 Nature 250-52 (1980); and Turkington, 57 Exper. Cell Res. 79-85 (1969). The disclosures cited in this paragraph are incorporated here by reference.

OBJECTIVES OF THE INVENTION

It is an object of this invention to provide a method which enhances the growth of mammary parenchyma in a female mammal, and thereby significantly increases the milk production capacity and/or efficiency of such a mammal. Another object is such a method having a high degree of specificity in the mammal for the desired increase in parenchyma. Another object is a method requiring use of a small (preferably minimal or near-minimal) quantity of a substance effecting such an enhancement in parenchyma growth. Another object is such a method which can be carried out conveniently. Another object is a method that provides predictably uniform growth-enhancement effects on treated mammary glands in the animal. Another object is a method having little potential for biological side effects in the animal. Other objects are various compositions suitable for convenient and commercially practical use in such methods. These and other objects of the invention will be more fully apparent from the following detailed disclosure.

SUMMARY OF THE INVENTION

We have discovered that these objectives can be achieved in female mammals by intramammary infusion of a substance having a mitogenic effect on mammary epithelial cells in that mammal. Surprisingly, substantial enhancement of normal parenchyma growth can be achieved by this method which does not require administration into the animal's blood stream, subcutaneous injection or implantation, but instead utilizes a convenient administration technique of a kind which, in the case of most dairy cows and some other mammals, has been routinely carried out for infusion of antibiotics. Substantial enhancements of parenchyma growth, and consequently milk production capacity of the mammal over those normally observed can be achieved by this invention utilizing only very small quantities of such substances, and in relatively short intervals of time. These discoveries were quite unexpected, largely because there was no prior art known to indicate that such substances would readily pass from the teat cistern of a mammary gland into contact with cells subject to the mitogenic effects needed to substantially enhance growth of the gland.

DESCRIPTION OF THE INVENTION

This invention is useful for any female mammal in which an increase in mammary parenchyma growth is desired. It is especially useful for ruminants, including cattle such as dairy cows, cows bred primarily for beef production, and heifers of dairy and beef cattle breeds. It is useful in all known breeds of dairy cows, e.g. Holstein, Friesien, Brown Swiss, Jersey, Guernsey, Ayrshire, Milking Shorthorn, and crossbreeds thereof, and in all known breeds of beef cows, e.g. Hereford, Angus, Zebu, Charolais, Brangus, Simmental, Chianina, Dutch Belted, Limousin, and crossbreeds thereof. It is also useful in other ruminants, e.g. sheep and goats of all breeds, as well as various non-ruminants, e.g. swine of all breeds. Most commonly, the invention is used for treatment of mammals that are physiologically normal which, for present purposes, means not ovariectomized and not pretreated (e.g. with a reproductive hormone such as estrogen, gonadotrophin or the like) to induce pseudopregnancy or puberty.

As used herein, the term "mammary parenchyma" refers to tissue in a mammary gland (including that commonly called "mammary epithelium") which is instrumental in production of milk by that gland. Typically in the female, mammary gland growth occurs mainly after the onset of puberty. Usually (e.g. in the heifer) most mammary gland growth occurs during the first gestation. Further growth and/or regrowth of the parenchyma occurs during subsequent gestations. Normally, the mitosis (cell division) causing such growth must be accompanied or followed by sufficient differentiation of the new cells that, following parturition, they will contribute to milk production.

To enhance such growth, this invention can be carried out by administering the substance having the desired mitogenic effect to the mammal between about the onset of puberty (including the peripubertal period) and the mammal's first gestation, or during the first or any subsequent gestation. Thus, typically such administration is carried out in a "dry" period, i.e., while the mammal is non-lactating. In pregnant dairy cows and similar mammals, administration during the last trimester before parturition is usually advantageous. The most preferred intervals for such administration depend on various factors, including the particular substance employed to achieve the desired mitogenic effect. Further details useful in identifying such preferred intervals are set forth hereinafter.

The convenient and surprisingly effective administration technique of this invention is most commonly called intramammary infusion. In mammals such as cows, this technique is routinely used to administer antibiotic-containing ointments or other formulations for prevention or control of mastitis. In practice of this invention, the substance having a mitogenic effect usually can be administered by a similar technique or, even more conveniently, by including it (with or without another parenchyma growth stimulant) in a formulation to be infused for mastitis prevention or control, or for any other purpose.

In this technique, a blunt-tip syringe is inserted through the teat orifice and streak canal such that the substance having a mitogenic effect is deposited in the teat cistern. From there, it normally spreads through the teat cistern, gland cistern and ductal system of the mammary gland. This well-known technique is described in "Drugs in Veterinary Practice", pp. 80-83, by Spinelli et al, C. V. Mosby Co., St. Louis, Mo. (1978) and U.S. Pat. No. 4,011,312 issued Mar. 8, 1977 to Reuter et al, both incorporated here by reference. For purposes of this invention, other procedures should be considered equivalents of intramammary infusion to the extent they deposit such a substance in the teat cistern and thereby result in spreading of same through the ductal system and passage therefrom into mammary tissue where it has an enhancing effect on parenchyma growth.

For purposes of this application, "direct" and "paracrine" mitogenic effects are to be understood as effects that do not require, and in most instances do not involve, the infused substance entering the treated animal's blood stream in an amount that raises its concentration therein to a level sufficient to have, through endocrine regulation, a mitogenic effect of the desired magnitude on parenchyma cells in the animal. For a review of paracrine regulation of mammary gland growth, see Oka et al, 15(1) Clinics in Endocrin. and Metab. 79-97 (1986).

This invention can be carried out using any substance having a significant direct or paracrine mitogenic effect on mammary parenchyma in the mammal to be treated. Many important embodiments are carried out using a substance which acts directly on mammary parenchyma cells in the infused gland to increase their rate of normal cell proliferation. In other embodiments, the substance acts directly on non-parenchyma cells within the gland resulting in such cells providing, through a paracrine effect, a locally increased amount of a substance having a direct mitogenic effect on mammary parenchyma cells in the infused gland.

In some instances, as can be seen from Examples 14-16 hereinafter, intramammary infusion of such a substance results in substantial growth of mammary glands adjacent to those infused, and without a significant increase in the level of the infused substance in the animal's bloodstream. However, sufficient receptors for direct or paracrine effects of some substances within a mammary gland may exist only during certain phases of the animal's physiology. For example, there appear to be a greater number of somatotropin-binding receptors in the bovine mammary gland during gestation than when the animals are not pregnant. Compare L'HORMONE PLACENTAIRE SOMATOMAMMOTROPE BOVINE (Chapter V) by Jean-Francois Beckers, Universite de Liege, Faculte de Medecine Veterinaire (1983) with Hormonal Control of Casein Synthesis and Organ Culture of the Bovine Lactating Mammary Gland, Gertler et al, 49 J. Dairy Res. 387 (1982) and Lactogenic Hormones: Binding Sites, Mammary Growth, Secretory Cell Differentiation, and Milk Biosynthesis in Ruminants, Akers, 68 J. Dairy Sci. 501 (1985).

In many embodiments of the invention, the substance having a mitogenic effect is a polypeptide growth factor. Certain classes of such growth factors preferred for use in this invention have molecular weights generally lower than about 65,000, even more typically lower than about 23,000 and, in the case of growth factors having a direct mitogenic effect as described hereinbefore, typically lower than about 10,000. Some non-polypeptide substances, e.g. ovarian and placental steroids and agonists thereof, can be suitably employed in some instances. In either case, the substance may be naturally occurring, synthesized to simulate a naturally occurring substance, or synthesized to provide a substance that is unlike any naturally occurring compound but nevertheless has such a mitogenic effect.

A preferred class of polypeptide growth factors that can be used are the epidermal growth factors (EGF's). Typically, these interact with receptors on mammary epithelial cells to stimulate proliferation of such cells. EGF's of various mammalian species have been sequenced and identified by their amino acid sequences and/or configurations dictated by internal cross-linking of cysteine residues through disulfide bonds. One such EGF is a well-characterized single-chain polypeptide of 53 amino acids which can be isolated from submaxillary (salivary) glands of adult male mice. Another form of EGF, human urogastrone, is synthesized in the duodenum and salivary glands and can be isolated from human urine. Urogastrone is 70% homologous (37 of 53 common amino acids) with mouse EGF and has three disulfide bonds in the same positions. Available data indicate that human urogastrone and human EGF are identical. Bovine EGF, which can be synthesized chemically or in a microorganism (e.g. bacteria such as *E. coli*) or eucaryotic cell culture by use of recombinant DNA, is believed to have an amino acid sequence essentially as follows: Asn-Phe-Leu-Lys-Lys-Cys-Phe-Pro-Glu-Tyr-Thr-Pro-Asn-Phe-Glu-Gly-Tyr-Cys-Leu-Asn-Gly-His-Val-Cys-Ile-Tyr-Phe-Gly-Ile-Ala-Asn-Leu-Phe-Ser-Cys-His-Cys-Pro-Ile-Gly-Tyr-Pro-Gly-Lys-Arg-Gly-Glu-Tyr-Ile-Asp-Phe-Asp-Gly-Trp-Asp-Pro-His. For more information on EGF's, see "Epidermal Growth Factor" by Carpenter et al, 48 Ann. Rev. Biochem. 193-216 (1979) and Gregory, 257 Nature 325-27 (1975), both incorporated here by reference.

It is known that the entire amino acid sequence of human or mouse EGF is not necessary for mitogenic activity. E.g., U.S. Pat. No. 3,917,824 issued Nov. 4, 1975 to Gamble et al discloses molecular variations shortened (e.g. by 2, 5 or 6 amino acids) at the carboxy terminus; U.S. Pat. No. 4,035,485 issued Jul. 12, 1977 to Gregory et al discloses a molecular variation shortened by 7 amino acids; U.S. Pat. No. 3,948,875 issued Apr. 6, 1976 to Cohen discloses EGF derivatives lacking the C-terminal Leu-Arg residues; PCT Appln. WO 83/04030 by Banks et al discloses urogastrone analogs that differ in identity or location of one or more amino acids; and PCT Appln. WO 85/01284 by Komoriya et al discloses polypeptides having EGF-like activity based on the presence of a ten-amino acid sequence corresponding to that between $Cys_{20}$ and $Cys_{31}$ of natural EFG; each incorporated herein by reference. To the extent these or similar molecular variations of EGF, analogs thereof, or other compounds that interact with EGF (or functionally similar) receptors in the mammary gland following intramammary infusion and achieve objectives of this invention in substantial measure, they are equivalents of EGF's for purposes of this invention.

Various procedures for preparing an EGF are known. E.g., Japanese Patent Appln. No. 59/027858 (Nippon Shinyaku) discloses condensing protected 1-5 amino acid peptides to form a protected tripentacontapeptide which is oxidized, after being deprotected, to make an EGF; European Patent Appln. 128,733 by Lee et al published Dec. 19, 1984 and Patent Appln. WO 85/00369 by Bell published Jan. 31, 1985 disclose EGF preparations by expression of recombined DNA; British Pat. No. 2,092,155 to Sugimoto discloses production of an EGF by multiplying hybridoma cells; and U.S. Pat. No. 4,528,186 issued Jul. 9, 1985 to Nishimura et al discloses recovery of an EGF from human urine. These disclosures are incorporated by reference.

In other preferred embodiments, the growth factor can be selected from fetal EGF's such as the alpha-type transforming growth factors. See European Patent Applns. Nos. 105,014 by Sporn et al and 190,018 by Todaro et al (disclosures incorporated here by reference). Typically, these interact with receptors in the mammary gland to provide the desired mitogenic activity. Another class of the various polypeptides useful in this invention is illustrated by the viral protein analogs disclosed in European Patent Appln. 199,769 based on WO 86/02650 by Brown et al.

In other embodiments, the growth factor can be a polypeptide from the insulin family, an analog of such a polypeptide, or another substance that interacts with insulin-like growth factor (IGF) or functionally similar receptors in the mammary gland to provide a mitogenic effect on the parenchyma. Preferably, the IGF employed is an IGF-I ("somatomedin") or IGF-II. Similar results can generally be obtained using insulin or a precursor thereof (e.g. pro-insulin) although the amounts required are much greater than those of an IGF.

There is extensive literature on identities of these insulin family growth factors and methods for their production. For example, amino acid sequences for human IGF-I and -II and their production by expression of recombinant DNA in microbial hosts are described in European Patent Applns. 128,733 (supra) and 123,228 (Chiron Corp.) published Oct. 31, 1984. IGF-I analogs having valine in amino acid position 59 are described in European Patent Appln. 158,892 by Niwa et al published Oct. 23, 1985. More information on IGF's can be found in Rinderknecht et al, 73 Proc. Natl. Acad. Sci. USA 2365 (1976); Zapf et al, 19 Curr. Top. Cell. Reg. 257 (1981); and Wilson et al, 95 J. Endocrin. 59-64 (1982). Preparations of insulin and pro-insulin are described in Johnson, 219 Sci. 632-37 (1983) and European Patent Appln. 55,945 (Genentech) published Jul. 14, 1982. The disclosures cited in this paragraph are incorporated here by reference.

In other preferred embodiments, the substance to be infused can be selected from one or a mixture of the various compounds in the arachidonic acid metabolic pathway and analogs thereof that have a mitogenic effect on mammary epithelial cells. These include the prostaglandins (such as those of the A to F series) and their analogs, e.g. [11α,13E,15S]-11,15-Dihydroxy-9-oxoprost-13-en-1-oic acid ($E_1$), [5Z,11α,13E,15S]-11,15-Dihydroxy-9-oxoprosta-5,13-dien-1-oic acid ($E_2$), [13E,15S]-15-Hydroxy-9-oxoprosta-10,13-dien-1-oic acid ($A_1$), [5Z,13E,15S]-15-Hydroxy-9-oxoprosta-5,10,13-trien-1-oic acid ($A_2$), [13E,15S]-15-Hydroxy-9-oxoprosta-8[12],13-dien-1-oic acid ($B_1$), [5Z,13E, 15S]-15-Hydroxy-9-oxoprosta-5,8[12],13-trien-1-oic acid ($B_2$), [5Z,9α,13E,15S]9,15-Dihydroxy-11-oxoprosta-5,13-dien-1-oic acid ($D_2$), [9α,11α,13E, 15S]-9,11,15-Trihydroxyprost-13-en-1-oic acid ($F_1α$), [5Z,9α,11α,13E,15S]-6,9-Epoxy-11,15-dihydroxyprosta-5,13-dien-1-oic acid ($I_2$), all available from Sigma Chemical Co., St. Louis, Mo., Lutalyse® prostaglandin ($F_2α$) available from The Upjohn Co., Kalamazoo, Mich., and cloprostenol. Precursors and metabolites of these substances (e.g. arachidonic acid and its metabolites) that are similarly active in effecting mammary cell mitosis can also be used, and those with greater activity and/or longer half life can be used in correspondingly lower doses. Many of these substances are described in Advances in Prostaglandin, Thromboxane, and Leukotriene Research, Vol. 14 (especially pp. 1-43, 73-129 and 263-307) edited by J. E. Pike and D. R. Morton, Jr., Raven Press, New York, N.Y., (1985), and Prostaglandins and the Arachidonic Acid Cascade, Norman A. Nelson, et al, 60 Chem. Eng. News, p. 30 et seq (Aug. 16, 1982), both incorporated here by reference.

In other embodiments, the growth factor can be one or a mixture of the mammary-derived or mesenchyme-derived growth factor (MDGF) polypeptides described by W. R. Kidwell et al in 260(9) J. Biol. Chem. 5745-52 (1985) and 46 Cancer Res. 933-39 (February 1986), the disclosures of which are incorporated here by reference. These MGDF's can be obtained by purification from milk or mammary tumors in accordance with procedures disclosed in those publications.

Substances that can be infused to achieve a paracrine mitogenic effect include placental lactogens, certain anterior pituitary hormones such as somatotropins, and other polypeptides having sufficiently similar chemical structure to provide essentially similar mitogenic effect(s) for purposes of this invention. Placental lactogens of specified mammalian species can be obtained by purification from their placental tissues. Bovine placental lactogen, which can be synthesized by use of recombinant DNA in microorganisms or cell cultures, has the amino acid sequence essentially as follows:

Ala-Glu-Asp-Tyr-Ala-Pro-Tyr-Cys-Lys-Asn-Gln-
Pro-Gly-Asn-Cys-Arg-Ile-Pro-Leu-Gln-Ser-Leu-
Phe-Glu-Arg-Ala-Thr-Leu-Val-Ala-Ser-Asn-Asn-
Tyr-Arg-Leu-Ala-Arg-Glu-Met-Phe-Asn-Glu-
Phe-Asn-Lys-Gln-Phe-Gly-Glu-Gly-Lys-Asn-
Phe-Thr-Ser-Lys-Val-Ile-Asn-Ser-Cys-His-Thr-
Glu-Phe-Met-Thr-Thr-Pro-Asn-Asn-Lys-Glu-Ala-
Ala-Ala-Asn-Thr-Glu-Asp-Glu-Ala-Leu-Leu-
Arg-Leu-Val-Ile-Ser-Leu-Leu-His-Ser-Trp-Asp-
Glu-Pro-Leu-His-Gln-Ala-Val-Thr-Glu-Leu-Leu-
His-Arg-Asn-Gly-Ala-Ser-Pro-Asp-Ile-Leu-Ala-
Arg-Ala-Lys-Glu-Ile-Glu-Asp-Lys-Thr-Lys-Val-
Leu-Leu-Glu-Gly-Val-Glu-Met-Ile-Gln-Lys-Arg-
Val-His-Pro-Gly-Glu-Lys-Lys-Asn-Glu-Pro-Tyr-
Pro-Val-Trp-Ser-Glu-Lys-Ser-Ser-Leu-Thr-Ala-
Asp-Asp-Glu-Asp-Val-Arg-Gln-Thr-Ala-Phe-
Tyr-Arg-Met-Phe-His-Cys-Leu-His-Arg-Asp-Ser-
Ser-Lys-Ile-Ser-Thr-Tyr-Ile-Asn-Leu-Leu-Lys-
Cys-Arg-Phe-Thr-Pro-Cys.

Further information about bovine placental lactogen, its production and biological activity can be found in U.S. patent application Ser. No. 07/221,124 filed on Jul. 21, 1988 by John C. Byatt et al. Bovine, ovine, porcine, human and other somatotropins can be obtained by various published procedures including that described in European Patent Appln. No. 177,478 published Apr. 9, 1986 (see Examples 40–41).

As aforesaid, infusion of a substance having a mitogenic effect in accordance with this invention should be completed far enough in advance of parturition that the resulting mammary tissue has adequate opportunity to differentiate into milk-producing cells. For substances having a direct mitogenic effect, e.g. IGF's, EGF's, prostaglandins, MDGF's, TGF-α's, insulins and combinations thereof, such infusion is most advantageously completed prior to about the last 5 (preferably 10) days of the mammal's pregnancy. When the substance is one providing a paracrine mitogenic effect, e.g. a somatotropin, placental lactogen or a mixture thereof, its administration can usually be continued until about 5 days before parturition without significantly detracting from the desired effect, although such administration during about the last 10 days of pregnancy may not substantially enhance that effect.

The amounts of the mitogenic activity-providing substance required by the present invention are very small, indicating an unexpectedly high efficiency in their use. For substances having a direct mitogenic effect, useful units doses for infusion of a gland may be no more than about 100 micrograms, and smaller doses may be effective in some instances. Unit doses up to about 10 milligrams or more can usually be administered without interfering with the desired effects, but doses less than about 1 milligram are generally preferable for economic reasons. In the case of substances having a paracrine mitogenic effect, such unit doses can be as little as about 10 milligrams, and smaller doses can be effective in some cases. Unit doses of such substances up to about 200 milligrams or more can generally be used without intolerably diminishing the desired effect, but doses less than about 100 milligrams are usually economically preferred.

The most desirable doses, frequencies and numbers of infusions can be determined by routine experimentation. Commonly, spacing treatments over as long a period as possible tends to afford maximum results, provided sufficient time remains thereafter for differentiation of the new parenchyma cells before parturition. In many cases, from 1 to about 5 successive infusions provide good results. These can be suitably spaced by, e.g., from 1 to about 10 (preferably from 2 to about 5) days. The fact that substantial increases in parenchyma growth can be achieved in such short periods of time was quite unexpected and has considerable commercial significance. Satisfactory total doses, i.e., the sum of the successive infusions of an individual mammary gland during a gestation or puberty prior to gestation, are generally at least about 100 micrograms, typically less than about 50 milligrams, and often preferably less than about 5 milligrams of a substance providing a direct mitogenic effect. For a substance having a paracrine mitogenic effect, satisfactory, total doses are generally at least about 100 milligrams and typically less than about 500 milligrams.

Other substances that furnish effects essentially similar to those afforded by any of the various mitogenic activity-providing substances mentioned herein can be likewise used in this invention, if desired. While the invention can be practiced using a single mitogenic activity-providing substance, combinations of such substances may be advantageous in some instances. In many embodiments, it is desirable to infuse a mitogenic activity-providing substance corresponding closely to a substance naturally occurring in the species to be treated, e.g. a bovine EGF, IGF, placental lactogen and/or somatotropin for treatment of cattle. However, substances corresponding to those naturally occurring in other species are commonly also suitable.

Normally, the method of this invention is carried out using a composition adapted for administration to a mammal by intramammary infusion and containing an amount, effective to enhance the growth of mammary parenchyma in said mammal, of a substance having a mitogenic effect on mammary epithelial cells in that mammal. Such compositions should be physio-logically tolerable, preferably substantially non-irritating and essentially free of endotoxins. If desired, the mitogenic activity-providing substance can be infused as a solid which may be finely divided or compressed in an advantageous shape and size, e.g. for prolonged release in the teat cistern. In other embodiments, it is desirable to use a vehicle that is substantially liquid at the mammal's body temperature, and preferably also at the ambient temperatures of infusion. Whether the infused composition is solid or fluid, it is normally advantageous for it to include a vehicle that enhances diffusion of the mitogenic activity-providing substance through the mammary gland. In some, but not all cases, it is advantageous for the vehicle to be substantially water-soluble. In most cases, it is advantageous to use a vehicle in which the mitogenic activity-providing substance is substantially soluble.

The most desirable type and quantity of vehicle for infusion of the mitogenic activity-providing substance can be determined by routine experimentation. To illustrate, 1-10 ml of a liquid vehicle having a pH in the physiological range, e.g. a physiological saline solution, Freund's Incomplete Adjuvant or a vegetable (e.g. peanut or sesame) or mineral oil, is typically satisfactory. Emulsions of two or more of such vehicles are commonly advantageous. Appropriate stabilizers, e.g. mono- and/or disaccharides, sugar and alcohols or neutral amino acids, may be included if desired.

This invention also provides a process for preparing compositions useful for enhancing the growth of mammary parenchyma in a mammal. In a generic embodiment, such a process comprises combining (e.g. dispersing) a substance having a mitogenic effect on mammary epithelial cells in said mammal in a vehicle that enhances diffusion (and preferably prolongs release) of the substance through a mammary gland of said mammal, said composition being adapted by said combining for administration to the mammal by intramammary infusion.

The following descriptions of specific embodiments of the invention are illustrative only and do not imply any limitation on the scope of the invention. All animals in these examples were physiologically normal (as defined hereinbefore). All temperatures are in degrees Celsius. Parts and percentages are by weight except where otherwise indicated.

A. Epidermal Growth Factors

EXAMPLES 1-2

12 pregnant, non-lactating, cross-bred beef cows within their last 40-80 days of gestation were housed in a free-stall facility, fed a ration of alfalfa hay and pelleted concentrate, and administered 10 ml of an excipient (Freund's Incomplete Adjuvant emulsified with an equal volume of 0.9% sterile saline) into each quarter-udder by intramammary infusion through the streak canal on days 1, 3, 5, 7 and 9 of this study. Infusions were carried out using a 3.2 centimeter long, approximately 12 gauge, blunt-tipped plastic teat infusion cannula obtained from Jorgensen Laboratories, Loveland, Colo. Because front and rear udder halves are not of equal size, treatment vs. control comparisons were made between laterally opposite quarters, i.e., front right vs. front left and rear right vs. rear left. Treatments were randomly assigned to right or left udder-halves, with the contralateral half serving as its control. In the treatment infusions, the excipient contained 25 micrograms of human EGF (hEGF) obtained from G. D. Searle & Co., Ltd., U.K. (6 animals) or mouse EGF (mEGF) obtained from Collaborative Research Corp., Lexington, Mass. (the other 6 animals). The hEGF had been prepared by Searle by expression of recombinant DNA and subsequently further purified by filtration on a 10,000 MW filter to a purity above 90% determined by HPLC. The mEGF was culture-grade, Catalog No. 40001, from mouse submaxillary glands, prepared by the method of Savage et al, 247 J. Biol. Chem. 7609 (1972) with a purity of 98% determined on SDS polyacrylamide gel.

Prior to treatment, each animal was teatdipped for 3 consecutive days and each teat was pre-cleaned with 70% ethanol in water on the day of treatment. On day 14 the cows were sacrificed and their mammary glands excised. Each udder (milked out if necessary) was skinned, divided along the median suspensory ligament and then into front right, front left, rear right and rear left udder quarters. Each quarter-udder was ground, a representative 200 gm sample was homogenized with 4 times its volume of water, and the total homogenate volume of each was measured.

To determine dry weight of each quarter-udder, three 10 ml aliquots of a 1:5 diluted homogenate were placed in pre-weighed pans, dried overnight at 60° and then dried and weighed to a consistent value.

To determine dry fat-free tissue weight of each quarter-udder, three 5 ml aliquots of the undiluted homogenate were extracted by the method of Anderson, 41 J. Anim. Sci. 118 (1975) except that samples were placed in pre-weighed 25×150 mm glass centrifuge tubes and extracted overnight with 10 ml ethanol:ether (3:1), then centrifuged (5 min at 500 rpm) and the supernatant aspirated; an additional 10 ml aliquot of ethanol:ether was added for a second extraction; and the sample was dried under nitrogen until a consistent value was obtained.

DNA in each quarter-udder was determined by the method of Burton, 12B Methods in Enzymol. 163-66 (1968) using an assay solution of 15% trichloroacetic acid (TCA) in 2N HCl. In these determinations, aliquots of gland homogenate were diluted 1:5 with water and rehomogenized. Using triplicate 0.25 ml or 0.5 ml aliquots of these homogenates, each aliquot was mixed with 2 ml of the assay solution. After 30 min, the samples were centrifuged for 10 min at 3000 rpm and the resulting pellets were washed with 2 ml of a 10% solution of TCA in distilled water. After recentrifugation, the resulting pellets were disrupted in 2 ml of 0.5N perchloric acid and heated for 30 min at 70° to extract DNA. Samples were centrifuged and 1 ml of each resulting supernatant was placed in a 12×75 mm tube. After addition of 2 ml of a solution of 1.5 g diphenylamine and 1.5 ml $H_2SO_4$ in 100 ml glacial acetic acid (and 0.1 ml of 1.6% aqueous acetaldehyde per 20 ml reagent just prior to use), the samples were vortexed and incubated overnight at 27°. Calf thymus DNA was the standard.

TABLE 1

Effects of Intramammary Infusion of hEGF on Quarter-Udders in Pregnant Beef Cows

|  | Wet Weight, g | Dry Weight, g | Dry Fat-Free Weight, g | DNA, mg |
|---|---|---|---|---|
| A. Treatment Mean | 389.9 | 120.0 | 63.2 | 794.5 |
| B. Control Mean (Excipient only) | 357.3 | 111.4 | 58.3 | 710 |
| C. Mean Increase (A-B) | 32.6 | 8.6 | 4.9 | 84.5 |
| D. % Increase, (A-B)/B | 9.1 | 7.7 | 8.4 | 11.9 |
| E. Avg % Increase/Animal | 12.9 | 13.1 | 16.1 | 14.8 |
| F. Sig. Level of % Increase, p< | 0.01 | 0.09 | 0.16 | 0.06 |

TABLE 2

Effects of Intramammary Infusion of mEGF on Quarter-Udders in Pregnant Beef Cows

|  | Wet Weight, g | Dry Weight, g | Dry Fat-Free Weight, g | DNA, mg |
|---|---|---|---|---|
| A. Treatment Mean | 419.6 | 150.2 | 69.6 | 905.1 |
| B. Control Mean (Excipient only) | 402.0 | 147.9 | 64.6 | 794.9 |
| C. Mean Increase | 17.6 | 2.3 | 5.0 | 110.2 |

TABLE 2-continued

Effects of Intramammary Infusion of mEGF on Quarter-Udders in Pregnant Beef Cows

|  | Wet Weight, g | Dry Weight, g | Dry Fat-Free Weight, g | DNA, mg |
|---|---|---|---|---|
| (A-B) |  |  |  |  |
| D. % Increase, (A-B)/B | 4.4 | 1.6 | 7.9 | 13.8 |
| E. Avg % Increase/Animal | 1.8 | 2.1 | 5.2 | 12.0 |
| F. Sig. Level of % Increase, p< | 0.22 | 0.40 | 0.19 | 0.05 |

As shown in Tables 1 and 2, quarter-udders infused with hEGF or mEGF were consistently heavier and contained more DNA than their laterally-opposite control quarters that received excipient only, and at generally high levels of statistical significance.

EXAMPLES 3-6

24 pregnant, non-lactating, cross-bred beef cows within their last 40-80 days of gestation were randomly divided into 4 treatment groups with 6 animals in each group. The effects of intramammary infusion of human EGF on quarter-udders in these animals were determined as described in Example 1 except that (A) as the excipient, the Freund's emulsion was used for Group 1 and an emulsion containing 60 parts sesame oil and 40 parts injectable grade 0.9% sterile saline containing 0.5% Tween-20 was used for Groups 2, 3 and 4 and (B) the amounts of hEGF included in each treatment infusion were 25 micrograms for Groups 1 and 2, 2.5 micrograms for Group 3, and 250 micrograms for Group 4. DNA determinations were made as in Examples 1-2 except that the initial triplicate 0.5 ml aliquots of homogenate were extracted with 2 ml of ethanol:ether (3:1) for 1 hour, centrifuged for 15 min at 3000 rpm, washed with 2 ml of 70% ethanol for 10 min, centrifuged at 3000 rpm for 15 min and aspirated of ethanol prior to mixing of each aliquot with the TCA solution. Results for Groups 1-4 are in Tables 3-6, respectively.

TABLE 3

Effects of Intramammary Infusion of a Total of 125 Micrograms of hEGF in Freund's Emulsion on Quarter-Udders in Pregnant Beef Cows (Group 1)

|  | Wet Weight, g | Dry Weight, g | Dry Fat-Free Weight, g | DNA, mg |
|---|---|---|---|---|
| A. Treatment Mean | 364.9 | 107.2 | 60.3 | 723.0 |
| B. Control Mean (Excipient only) | 349.5 | 101.0 | 56.8 | 629.0 |
| C. Mean Increase (A-B) | 15.4 | 6.2 | 3.5 | 94.0 |
| D. % Increase, (A-B)/B | 4.4 | 6.1 | 6.2 | 14.9 |
| E. Avg % Increase/Animal | 8.1 | 10.3 | 8.3 | 23.0 |
| F. Sig. Level of % Increase, p< | 0.15 | 0.11 | 0.13 | 0.18 |

TABLE 4

Effects of Intramammary Infusion of a Total of 125 Micrograms of hEGF in Sesame Emulsion on Quarter-Udders in Pregnant Beef Cows (Group 2)

|  | Wet Weight, g | Dry Weight, g | Dry Fat-Free Weight, g | DNA, mg |
|---|---|---|---|---|
| A. Treatment Mean | 370.2 | 122.1 | 71.0 | 995.0 |
| B. Control Mean (Excipient only) | 356.2 | 111.1 | 68.8 | 703.0 |
| C. Mean Increase (A-B) | 14.0 | 11.0 | 2.2 | 292.0 |
| D. % Increase, (A-B)/B | 3.9 | 9.9 | 3.2 | 41.5 |
| E. Avg % Increase/Animal | 10.4 | 20.2 | 15.9 | 70.0 |
| F. Sig. Level of % Increase, p< | 0.2 | 0.02 | 0.3 | 0.09 |

TABLE 5

Effects of Intramammary Infusion of a Total of 12.5 Micrograms of hEGF in Sesame Emulsion on Quarter-Udders in Pregnant Beef Cows (Group 3)

|  | Wet Weight, g | Dry Weight, g | Dry Fat-Free Weight, g | DNA, mg |
|---|---|---|---|---|
| A. Treatment Mean | 397.8 | 132.4 | 79.4 | 867.6 |
| B. Control Mean (Excipient only) | 400.0 | 127.0 | 72.7 | 896.6 |
| C. Mean Increase (A-B) | (2.2) | 5.4 | 6.7 | (29.0) |
| D. % Increase, (A-B)/B | (0.5) | 4.2 | 9.2 | (3.3 |
| E. Avg % Increase/Animal | 0.6 | 7.8 | 16.3 | (2.2) |
| F. Sig. Level of % Increase, p< | — | 0.17 | 0.1 | — |

TABLE 6

Effects of Intramammary Infusion of a Total of 1.25 Milligrams of hEGF in Sesame Emulsion on Quarter-Udders in Pregnant Beef Cows (Group 4)

|  | Wet Weight, g | Dry Weight, g | Dry Fat-Free Weight, g | DNA, mg |
|---|---|---|---|---|
| A. Treatment Mean | 391.9 | 131.5 | 81.7 | 733.2 |
| B. Control Mean (Excipient only) | 360.2 | 117.9 | 75.1 | 729.2 |
| C. Mean Increase (A-B) | 31.7 | 13.6 | 6.6 | 4.0 |
| D. % Increase, (A-B)/B | 8.8 | 11.6 | 8.8 | 0.5 |
| E. Avg % Increase/Animal | 9.9 | 12.2 | 11.9 | 1.6 |
| F. Sig. Level of % Increase, p< | 0.001 | 0.004 | 0.03 | — |

As shown in Tables 3-6, quarter-udders infused with hEGF were generally substantially heavier and contained more DNA than their laterally-opposite quarters that received excipient only.

EXAMPLES 7-8

24 pregnant, non-lactating, cross-bred beef cows within their last 40-80 days of gestation were randomly divided into 3 treatment groups with 8 animals in each group. The effects of intramammary infusion of human EGF on quarter-udders in these animals were determined as described in Examples 1-2 except that the amounts of hEGF included in each treatment infusion were 25 micrograms for Group 1, 250 micrograms for Group 2, and 2.5 micrograms for Group 3. Gland weights and DNA were determined as in Examples 1-2. Results with the low dose used for Group 3 were obscured by swellings of some glands. Results for Groups 1 and 2 are in Tables 7 and 8, respectively.

TABLE 7

Effects of Intramammary Infusion of a Total of 125 Micrograms of hEGF on Quarter-Udders in Pregnant Beef Cows (Group 1)

|  | Wet Weight, g | Dry Weight, g | Dry Fat-Free Weight, g | DNA, mg |
|---|---|---|---|---|
| A. Treatment Mean | 363.0 | 113.0 | 52.8 | 396.9 |
| B. Control Mean (Excipient only) | 358.0 | 109.7 | 50.7 | 358.9 |
| C. Mean Increase (A-B) | 5.0 | 3.3 | 2.1 | 38.0 |
| D. % Increase, (A-B)/B | 1.5 | 3.0 | 4.1 | 10.6 |
| E. Sig. Level of % Increase, $p<$ | 0.34 | 0.21 | 0.16 | 0.12 |

TABLE 8

Effects of Intramammary Infusion of a Total of 1.25 Milligrams of hEGF on Quarter-Udders in Pregnant Beef Cows (Group 2)

|  | Wet Weight, g | Dry Weight, g | Dry Fat-Free Weight, g | DNA, mg |
|---|---|---|---|---|
| A. Treatment Mean | 392.5 | 122.0 | 63.8 | 344.0 |
| B. Control Mean (Excipient only) | 388.2 | 115.7 | 61.4 | 384.0 |
| C. Mean Increase (A-B) | 4.3 | 6.3 | 2.4 | (40.0) |
| D. % Increase, (A-B)/B | 1.1 | 5.3 | 3.9 | (10.4) |
| E. Sig. Level of % Increase, $p<$ | 0.4 | 0.12 | 0.26 | — |

As shown in Tables 7-8, quarter-udders infused with hEGF were heavier than their laterally-opposite quarter-udders that received excipient only.

EXAMPLES 9-12

When dairy or beef heifers (either pregnant or non-pregnant) or pregnant dairy or beef cows within their last 25-60 days of gestation are infused using the procedures and dosages of Examples 3-6 with bovine EGF, results are essentially the same, i.e. substantial and statistically significant increases in the weights and DNA of the treated quarter-udders.

EXAMPLE 13

48 pregnant Holstein heifers within their last 40 days (approximately) of gestation were housed in a free-stall facility, fed a ration of alfalfa hay and pelleted concentrate, and administered 10 ml of an excipient into each quarter-udder by intramammary infusion through the streak canal every third day until parturition with the exception of one animal which was treated with human EGF as described in this Example only until 15 days before parturition. Infusions were carried out using a 3.2 centimeter long, approximately 12 gauge, blunt-tipped plastic teat infusion cannula obtained from Jorgensen Laboratories, Loveland, Colo. Animals were randomly assigned to each of the following 4 treatments (12 animals each): (A) 250 micrograms of human EGF obtained from G. D. Searle & Co., Ltd. (U.K.), solubilized (62.5 micrograms/ml) in sterile, injectable grade 0.9% saline containing 0.5% Tween-20 and then emulsified just prior to use in sterile sesame oil containing 5% Arlacel A mannide monooleate (3:2 oil:saline) with a final concentration of 25 micrograms/ml of hEGF in the excipient; (B) 250 micrograms of bovine IGF-I prepared as in Examples 14-16, purified and then solubilized and emulsified as just described for hEGF; (C) 50 milligrams of N-methionyl bovine somatotropin (BST) prepared as in Examples 40-41 and then diluted to 10 mg/ml in sterile sesame oil; and (D) a control using excipient (sterile sesame oil) alone. In each animal, all 4 quarter-udders received the same treatment. Each udder was sprayed with 70% ethanol and wiped dry prior to treatment and dipped with an iodine solution following treatment. At parturition, 4 animals from each treatment group were sacrificed and their mammary glands were removed for analysis. The other 8 animals from each treatment group were milked normally each a.m. and p.m. for the first 105 days of lactation.

During those 105 days, the animal treated with hEGF only until 15 days before parturition produced an average of 9.6 kg milk/day (34.8%) more than the average produced by the 8 control cows. On average, milk production by the cows treated until parturition did not exceed that of the control cows.

B. Insulin-like Growth Factors

EXAMPLES 14-16

24 pregnant, non-lactating, cross-bred beef cows within their last 40-80 days of gestation were housed in a free-stall facility, fed a ration of alfalfa hay and pelleted concentrate, and administered 10 ml of an excipient (a sesame oil emulsion of the kind used in Examples 4-6) into each half-udder by intramammary infusion through the streak canal on days 1, 3, 5, 7 and 9 of this study. The infusion technique, random assignment of half-udders to treatment or control, and treatment vs. control comparisons were as in Examples 1-2. In the treatment infusions, the excipient contained bovine insulin-like growth factor-I (bIGF-I) prepared by expression in *E. coli* (Prla Strain 079) of recombinant DNA coding for bIGF-I fused to the "lam" B cell wall protein signal sequence, secretion into the *E. coli* periplasmic space, and recovery/purification by conventional techniques including gel filtration, cation exchange and reverse-phase HPLC. This bIGF-I had the same amino acid sequence and secondary structure as the AMgen human IGF-I used in Example 20. In standard L6 myoblast assays, its activity was essentially the same (90-123%) as that of the Example 20 hIGF-I. The amounts of bIGF-I in each infusion were: Group 1-2.5 micrograms: Group 2-25 micrograms; Group 3-250 micrograms. Animals were prepared and infused, and their quarter-udder weights and DNA were determined as in Example 3-6. Results for Group 1 are in Table 9.

TABLE 9

Effects of Intramammary Infusion of a Total of 12.5 Micrograms of bIGF-I on Quarter-Udders in Pregnant Beef Cows (Group 1)

| | Wet Weight, g | Dry Weight, g | Dry Fat-Free Weight, g | DNA, mg |
|---|---|---|---|---|
| A. Treatment Mean | 408.4 | 111.7 | 54.9 | 1307 |
| B. Control Mean (Excipient only) | 369.0 | 102.7 | 48.0 | 1219 |
| C. Mean Increase (A-B) | 39.4 | 9.0 | 6.9 | 88 |
| D. % Increase, (A-B)/B | 10.7 | 8.7 | 14.2 | 7.2 |
| E. Avg % Increase/Animal | 11.0 | 8.8 | 16.0 | 12.5 |
| F. Sig. Level of % Increase, $p <$ | 0.01 | 0.003 | 0.03 | 0.2 |

In this study, the two higher doses of bIGF-I (Groups 2-3) did not produce consistently greater growth of treatment quarters vs. control quarters. However, substantial growth of the non-infused quarters was observed. When the procedures described for Groups 1-3 were repeated, results were essentially the same. Pooling results from the original study and its replication, it was determined that both treatment and control quarter-udders had grown as follows:

TABLE 10

| Doses | Controls | Treatment | Combined |
|---|---|---|---|
| Medium vs. Low | +27%, $p < 0.08$ | +23.1%, $p < 0.12$ | +25% |
| High vs. Medium | +34.4%, $p < 0.08$ | +31.5%, $p < 0.09$ | +33% |
| High vs. Low | +71.3%, $p < 0.007$ | +62%, $p < 0.01$ | +67% |

The above increases in growth of the control quarter-udders occurred even though plasma levels of bIGF-I did not increase significantly during the study. Results were essentially the same when these tests were repeated using other pregnant, non-lactating beef cows grouped on the basis of essentially equal beginning udder volumes to remove that variable as much as possible from the test results.

EXAMPLES 17-19

When dairy or beef heifers (either pregnant or non-pregnant) or pregnant cows within their last 25-60 days of gestation are infused according to the procedure in Examples 14-16 with a total of 125 micrograms, 1.25 milligrams or 12.5 milligrams of bovine insulin-like growth factor-II purified essentially free from all other bovine peptides as in Example 1 of U.S. Pat. application No. 888,996 filed Jul. 31, 1986 corresponding to European Patent Appln. 86870128.5, both incorporated herein by reference, the results are essentially the same as in Examples 14-16, i.e., substantial increases in the weights and DNA of the treated quarter-udders.

C. Combinations of IGF's and EGF's

EXAMPLE 20

30 mixed-breed sheep within their last 35-45 days of gestation were fed a ration of alfalfa hay and sheep chow and administered 2.5 ml of an excipient (a Freund's emulsion of the kind used in Examples 1-2 for 15 sheep; physiological (0.9%) saline solution for the other 15) into each half-udder by intramammary infusion through the streak canal on days 1, 3, 5, 7 and 9 of this study. Infusions were carried out using a 3.2 centimeter long, 16 gauge, blunt-tipped Teflon sheath from a C. R. Bard, Inc. A-cath cannula for placement of indwelling catheters. Udder halves in each animal were randomly assigned to treatment in which the excipient contained additionally 2.5 micrograms of mouse EGF of the kind used in Examples 1-2 and 2.5 micrograms of human IGF-I prepared by expression of recombinant DNA and sold by AMgen Biological Corp., Thousand Oaks, Calif. (Catalog No. 04111, Lot 407; over 90% pure as determined by HPLC). The other udder half in each animal was assigned to control in which the excipient only was infused. Prior to treatment, each animal was teat-dipped for 7 consecutive days and each teat was pre-cleaned with 70% ethanol in water on the day of treatment.

On day 13 the sheep were sacrificed and their mammary glands excised. Each udder (milked out if necessary) was skinned and divided along the median suspensory ligament into right and left udder halves. Each half-udder was homogenized with 4 times its weight of water, and the total homogenate volume of each was measured.

To determine dry weight of each half-udder, three 10 ml aliquots of a 1:5 diluted homogenate were placed in pre-weighed pans, dried overnight at 60° and then dried and weighed to a consistent value.

To determine dry fat-free tissue weight of each half-udder, three 5 ml aliquots of the undiluted homogenate were extracted by the method of Anderson, 41 J. Anim. Sci. 118 (1975) except that samples were placed in pre-weighed 25×150 mm glass centrifuge tubes and extracted overnight with 10 ml of ethanol:ether (3:1), then centrifuged (5 min at 500 rpm) and the supernatant aspirated; an additional 10 ml aliquot of ethanol:ether was added for a second extraction; and the sample was dried under nitrogen and weighed until a constant value was obtained.

DNA in each half-udder was determined by the method of Burton, Biochemistry 62315 (1956) using an assay solution of 15% trichloroacetic acid (TCA) in 2N HCl. In these determinations, aliquots of gland homogenate were thawed, diluted 1:5 with water and rehomogenized. Using triplicate 0.5 ml aliquots of these homogenates, each aliquot was mixed with 2 ml of the assay solution. After 30 min, the samples were centrifuged for 10 min at 3000 rpm and the resulting pellets were washed with 2 ml of a 10% solution of TCA in distilled water. After recentrifugation, the resulting pellets were disrupted in 2 ml of 0.5N perchloric acid and heated for 30 min at 70° to extract DNA. Samples were centrifuged and 1 ml of each resulting supernatant was placed in a 12×75 mm tube. After addition of 2 ml of a solution of 1.5 g diphenylamine and 1.5 ml $H_2SO_4$ in 100 ml glacial acetic acid (and 0.1 ml of 1.6% aqueous acetaldehyde per 20 ml reagent just prior to use), the samples were vortexed and incubated overnight at 20°. Calf thymus DNA was the standard.

Results are in Table 11.

TABLE 11

Effects of Intramammary Infusion of a Combination of mEGF and hIGF-I on Half-Udders in Pregnant Sheep

| | Wet Weight, g | Dry Weight, g | Dry Fat-Free Weight, g | DNA, mg |
|---|---|---|---|---|
| A. Treatment | 277.3 | 73.6 | 75.2 | 1021.2 |

TABLE 11-continued

Effects of Intramammary Infusion of a Combination of mEGF and hIGF-I on Half-Udders in Pregnant Sheep

| | Wet Weight, g | Dry Weight, g | Dry Fat-Free Weight, g | DNA, mg |
|---|---|---|---|---|
| Mean | | | | |
| B. Control Mean (Excipient only) | 264.7 | 66.2 | 56.4 | 849.5 |
| C. Mean Increase (A-B) | 12.5 | 7.4 | 18.8 | 171.7 |
| D. % Increase, (A-B)/B | 4.7 | 11.0 | 33.0 | 20.2 |
| E. Sig. Level of % Increase, p< | 0.016 | 0.03 | 0.001 | 0.002 |

The data in Table 11 show that DNA and wet, dry and dry fat-free weights of the half-udders treated in accordance with this invention were substantially increased relative to the untreated half-udders in the same animals, and at exceptionally high levels of statistical significance.

EXAMPLE 21

8 non-pregnant Holstein heifers about 18 months of age were tested for the effects of intramammary infusion of a combination of bovine IGF-I and human EGF according to the procedures used in Examples 14–16 with the exceptions that (A) the volume of excipient in each infusion was 2.5 ml, (B) each treatment infusion contained 6.25 micrograms of bIGF-I and 625 micrograms of hEGF of the kinds used in Examples 14–16 and 1–2, respectively, and (C) DNA's were not determined. Results are in Table 12.

TABLE 12

Effects of Intramammary Infusion of a Combination of hEGF and bIGF-I on Quarter-Udders in Holstein Heifers

| | Wet Weight, g | Dry Weight, g | Dry Fat-Free Weight, g |
|---|---|---|---|
| A. Treatment Mean | 205.1 | 93.2 | 10.7 |
| B. Control Mean (Excipient only) | 188.2 | 89.0 | 9.5 |
| C. Mean Increase (A-B) | 16.9 | 4.2 | 1.2 |
| D. % Increase (A-B/B) | 8.9 | 4.7 | 12.1 |
| E. Avg. % Increase/Animal | 11.3 | 7.7 | 18.8 |
| F. Sig. Level of Increase, p< | 0.06 | 0.2 | 0.09 |

The data in Table 12 shows that the wet, dry and dry fat-free weights of Holstein heifer quarter-udders treated in accordance with this invention were substantially greater than their laterally-opposite quarter-udders that received excipient only, and at high levels of statistical significance.

EXAMPLE 22

The effects of intramammary infusion of a combination of bovine IGF-I and human EGF on 8 pregnant, non-lactating, cross-bred beef cows within their last 40–80 days of gestation were determined by the procedures described in Examples 14–16. Each treatment infusion contained 25 micrograms of hEGF of the kind used in Examples 1–2 and 250 micrograms of bIGF-I of the kind used in Examples 14–16. Results are in Table 13.

TABLE 13

Effects of Intramammary Infusion of a Combination of bIGF-I (A Total of 1.25 Milligrams) and hEGF (a Total of 125 Micrograms) on Quarter-Udders in Pregnant Beef Cattle

| | Wet Weight, g | Dry Weight, g | Dry Fat-Free Weight, g | DNA, mg |
|---|---|---|---|---|
| A. Treatment Mean | 496.1 | 156.4 | 72.0 | 1392 |
| B. Control Mean (Excipient only) | 474.0 | 144.0 | 60.7 | 1243 |
| C. Mean Increase (A-B) | 22.1 | 12.4 | 11.3 | 149 |
| D. % Increase, (A-B)/B | 4.7 | 8.6 | 18.7 | 12.0 |
| E. Avg. % Increase/Animal | 8.2 | 13.0 | 11.0 | 12.0 |
| F. Sig. Level of % Increase, p< | 0.1 | 0.03 | 0.08 | 0.15 |

As shown in Table 13, quarter-udders receiving the combination of bIGF-I and hEGF were consistently heavier and contained more DNA than their laterally-opposite control quarters, and at high levels of statistical significance.

EXAMPLES 23–14

18 pregnant Holstein heifers within their last 40–60 days of expected calving were housed in a free-stall facility, fed a ration of alfalfa hay and pelleted concentrate and administered 10 ml of an excipient (sterile sesame oil) into each quarter-udder by intramammary infusion through the steak canal every third day for the number of treatments shown below. The heifers in Groups 1 and 3 were treated no later than their fifth day before parturition; treatments of those in Groups 2 and 4 were continued into their last five days. Treatments containing a mitogenic substance were administered to both quarter-udders on one side of each animal. Excipient only was administered to both quarter-udders on the opposite side of that animal. All infusions were carried out with a Jorgensen laboratories infusion canula of the kind used in Examples 1–2. Each teat was sprayed with 70% ethanol and wiped dry prior to treatment, and dipped with an iodine solution following treatment.

| Group | No. of Heifers | Mitogenic Substance In The Excipient | No. of Treatments Range | Avg. |
|---|---|---|---|---|
| 1 | 4 | hEGF & IGF-I* (0.25 mg each) | 10 | 10 |
| 2 | 5 | hEGF & IGF-I* (0.25 mg each) | 7–20 | 14 |
| 3 | 5 | BST** (50 mg) | 10–20 | 12 |
| 4 | 4 | BST** (50 mg) | 4–16 | 9 |

*Obtained as in Example 1-2 and 14-16, respectively, solubilized (62.5 micrograms/ml of each) in sterile, injectable-grade 0.9% saline containing 0.5% Tween-20 and emulsified into the sterile sesame oil excipient (3:2 oil: saline) and 5% Arlacel A (Sigma Chemical Co., St. Louis, MO).
**Prepared as in Examples 40–41 and diluted to 10 mg/ml in the sesame oil excipient. See results in Examples 42–43.

These animals were milked normally each a.m. and p.m. for the first 30 days after parturition, with milk production recorded separately for each quarter-udder. On average, milk production by the half-udders that had been treated in Group 2 did not exceed that of their control half-udders.

TABLE 14

Effects of Intramammary Infusion of a Combination of hEGF and IGF-I on Quarter-Udders in Pregnant Heifers (Group 1)

| Average Milk Production, kg/day | | | |
|---|---|---|---|
| Treated Side (A) | Control Side (B) | % Increase, (A-B)/B | Sig. Level of Increase, $p<$ |
| 10.0 | 9.0 | 11 | 0.14 |

As shown in Table 14, quarter-udders infused with a combination of hEGF and IGF-I no later than the fifth day before parturition produced, on average, substantially more milk than their laterally-opposite quarters that received excipient only.

D. Prostaglandins

EXAMPLES 25–28

24 pregnant, non-lactating, cross-bred beef cows in their last 45–105 days of gestation were housed in a free-stall facility, fed a ration of alfalfa hay and pelleted concentrate, and administered 5 ml of an excepient (MCT-Oil, a Mead Johnson Corp. medium chain triglyceride which is a lipid fraction of coconut oil consisting primarily of triglycerides of $C_8$ and $C_{10}$ fatty acids as follows: $C_8$-67%; $C_{10}$-23%; $<C_8$-6%; $>C_{10}$-4%) into each quarter-udder by intramammary infusion through the streak cannal on days 1, 3, 5, 7 and 9 of this study. The 48 front and rear udder halves were randomly divided into 4 groups, with one quarter of each udder half treated and its laterally opposite quarter-udder used as a control. In the treatment infusions, the excipient contained Prostaglandin (PG) $E_1$ or $E_2$ from Sigma Chemical Co., St. Louis, Mo. (Catalog Nos. 86F-0406 and -0404). The amounts of PG in each infusion were: Group 1-87.5 micrograms of $E_2$; Group 2-875 micrograms of $E_2$; Group 3-87.5 micrograms of $E_1$; Group 4-875 micrograms of $E_1$. Animals were prepared and infused as in Examples 23-24; the effects were determined as in Examples 1-2. Results for Groups 1-4 are in Tables 15-18, respectively.

TABLE 15

Effects of Intramammary Infusion of Prostaglandin $E_2$ (a Total of 0.4375 Milligrams) on Quarter-Udders in Pregnant Beef Cattle (Group 1)

| | Wet Weight, g | Dry Weight, g | Dry Fat-Free Weight, g | DNA, mg |
|---|---|---|---|---|
| A. Treatment Mean | 1966.9 | 525.5 | 351.8 | 5203 |
| B. Control Mean (Excipient Only) | 1735.5 | 484.9 | 297.8 | 4724 |
| C. Mean Increase (A-B) | 231.4 | 40.6 | 54.0 | 479 |
| D. % Increase (A-B)/B | 13.3 | 8.3 | 18.1 | 10.1 |
| E. Sig. Level of % Increase, $p<$ | 0.01 | 0.04 | 0.18 | 0.02 |

TABLE 16

Effects of Intramammary Infusion of Prostaglandin $E_2$ (a Total of 4.375 Milligrams) on Quarter-Udders in Pregnant Beef Cattle (Group 2)

| | Wet Weight, g | Dry Weight, g | Dry Fat-Free Weight, g | DNA, mg |
|---|---|---|---|---|
| A. Treatment Mean | 1030.8 | 312.7 | 194.5 | 3397 |
| B. Control Mean (Excipient Only) | 742.0 | 219.0 | 144.3 | 2348 |
| C. Mean Increase (A-B) | 288.8 | 93.7 | 50.2 | 1049 |
| D. % Increase, (A-B)/B | 38.9 | 42.8 | 34.8 | 44.6 |
| E. Sig. Level of % Increase, $p<$ | 0.0003 | 0.0001 | 0.004 | 0.001 |

TABLE 17

Effects of Intramammary Infusion of Prostaglandin $E_1$ (a Total of 0.4375 Milligrams) on Quarter-Udders in Pregnant Beef Cattle (Group 3)

| | Wet Weight, g | Dry Weight, g | Dry Fat-Free Weight, g | DNA, mg |
|---|---|---|---|---|
| A. Treatment Mean | 972.5 | 259.3 | 180.9 | 2881 |
| B. Control Mean (Excipient Only) | 778.0 | 210.6 | 200.3 | 2284 |
| C. Mean Increase, (A-B) | 194.5 | 48.7 | (19.4) | 597 |
| D. % Increase, (A-B)/B | 25.0 | 23.0 | (9.7) | 26 |
| E. Sig. Level % Increase, $p<$ | 0.002 | 0.002 | 0.58 | 0.07 |

TABLE 18

Effects of Intramammary Infusion of Prostaglandin $E_1$ (a Total of 4.375 Milligrams) on Quarter-Udders in Pregnant Beef Cattle (Group 4)

| | Wet Weight, g | Dry Weight, g | Dry Fat-Free Weight, g | DNA, mg |
|---|---|---|---|---|
| A. Treatment Mean | 1435.5 | 379.6 | 247.7 | 4218 |
| B. Control Mean (Excipient Only) | 949.3 | 268.2 | 189.0 | 2792 |
| C. Mean Increase (A-B) | 486.2 | 111.4 | 58.7 | 1426 |
| D. % Increase (A-B)/B | 51.2 | 41.5 | 31.0 | 51.1 |
| E. Sig. Level % Increase, $p<$ | 0.03 | 0.02 | 0.07 | 0.06 |

As shown in Tables 15–18, quarter-udders receiving the prostaglandins were consistently heavier and contained more DNA than their laterally-opposite control quarters that received excipient only, and at generally very high levels of statistical significance.

E. Transforming Growth Factors

EXAMPLES 29-32

When dairy or beef heifers (either pregnant or non-pregnant) or pregnant dairy or beef cows within their last 25-60 days of gestation are infused using the procedures and dosages of Examples 3-6 with human alpha-type transforming growth factor obtained from Bachem Inc. Fine Chemicals, Torrance, Calif. (Catalog #PGRO-30), results are essentially the same, i.e., substantial and statistically significant increases in the weights and DNA of the treated quarter-udders. The production and use of bovine transforming growth factor-alpha is grounded in the following Example J. herein.

F. Mammary-Derived Growth Factors

EXAMPLES 33-36

When dairy or beef heifers (either pregnant or non-pregnant) or pregnant beef or dairy cows within their last 25-60 days of gestation are infused using the procedures and dosages of Examples 3-6 with $MDGF_1$ or $MDGF_2$ obtained by purification according to the aforecited Kidwell et al publications, results are essentially the same, i.e., substantial and statistically substantial increases in the weight and DNA of the treated quarter-udders.

G. Insulin

EXAMPLES 37-39

When dairy or beef heifers (either pregnant or non-pregnant) or pregnant beef or dairy cows within their last 25-60 days of gestation are infused according to the procedures of Examples 3-6 with 25, 100 or 250 mg per infusion of bovine pancreas insulin from Sigma Chemical Co., St. Louis, Mo. (Catalog #I-5500; 24 IU/mg), results are similar, i.e., substantial and statistically significant increases in the weights and DNA of the treated quarter-udders.

H. Somatotropins

EXAMPLES 40-41

24 pregnant, non-lactating, cross-bred beef cows in their last 40-80 days of gestation were divided into 2 groups and tested for the effects of intramammary infusion using the procedures of Examples 3-6 except that (A) the volume of excipient in each infusion was 5 ml and (B) each treatment infusion contained a 1% zinc salt of an N-methionyl bovine somatotropin (BST) (Group 1-100 mg; Group 2-40 mg) prepared by expression of recombinant DNA and purified essentially as described in Example 1A of U.S. Patent Appln. No. 787,873 filed Oct. 16, 1985 based on European Patent Appln. No. 177,478 published Apr. 9, 1986, both incorporated here by reference. Results are in Tables 19-20.

TABLE 19

Effects of Intramammary Infusion of a Total of 500 Milligrams of BST on Quarter-Udders in Pregnant Beef Cows (Group 1)

|   | Wet Weight, g | Dry Weight, g | Dry Fat-Free Weight, g | DNA, mg |
|---|---|---|---|---|
| A. Treatment Mean | 790.1 | 207.6 | 146.7 | 2185 |
| B. Control Mean (Excipient only) | 736.6 | 190.6 | 141.5 | 2054 |
| C. Mean Increase (A-B) | 53.5 | 17.0 | 5.2 | 131 |
| D. % Increase, (A-B)/B | 7.3 | 8.9 | 3.6 | 6.4 |
| E. Avg. % Increase/ Animal | 9.8 | 10.7 | 7.9 | 10.5 |
| F. Sig. Level of % Increase, p< | 0.004 | 0.03 | 0.18 | 0.3 |

TABLE 20

Effects of Intramammary Infusion of a Total of 200 Milligrams of BST on Quarter-Udders in Pregnant Beef Cows (Group 2)

|   | Wet Weight, g | Dry Weight, g | Dry Fat-Free Weight, g | DNA, mg |
|---|---|---|---|---|
| A. Treatment Mean | 396.9 | 96.4 | 49.5 | 1371 |
| B. Control Mean (Excipient only) | 345.4 | 85.1 | 44.8 | 1299 |
| C. Mean Increase (A-B) | 51.5 | 11.3 | 4.7 | 72 |
| D. % Increase, (A-B)/B | 14.9 | 13.3 | 10.5 | 5.5 |
| E. Avg. % Increase/ Animal | 13.4 | 10.7 | 7.8 | 15.8 |
| F. Sig. Level of % Increase, p< | 0.007 | 0.06 | 0.06 | 0.1 | of pregnant beef cow quarter-udders treated in accordance with this invention were substantially greater than those of their laterally-opposite quarter-udders that received excipient only, and that the differences between treatment and control increases are at high levels of statistical significance.

EXAMPLES 42-43

Shown in Table 21 are the milk production results obtained with the heifers of Group 3 in Examples 23-24. On average, milk production by the half-udders that had been treated in Group 4 of Examples 23-24 slightly exceeded (2%, p<0.4) that of their control half-udders.

TABLE 21

Effects of Intramammary Infusion of BST on Quarter-Udders in Pregnant Holstein Heifers (Group 4)

| Average Milk Production, kg/day | | % Increase, (A-B)/B | Sig. Level of Increase, p< |
|---|---|---|---|
| Treated Side (A) | Control Side (B) | | |
| 10.9 | 9.8 | 11 | 0.15 |

As shown in Table 21, quarter-udders infused with BST no later than the fifth day before parturition produced, on average, substantially more milk than their laterally-opposite quarters that received excipient only.

I. Bovine Placental Lactogens

EXAMPLES 44-46

When dairy or beef heifers (either pregnant or non-pregnant) or pregnant beef or dairy cows within their last 40-80 days of gestation are infused according to the procedures of Examples 3-6 with a total of 0.25, 10 or 250 milligrams of natural bovine placental lactogen purified by the method of Byatt, 119 Endocrin. 1343-50 (1986), results are very similar, i.e., substantial and statistically significant increases in the weights and DNA of the treated quarter-udders.

COMPARATIVE EXAMPLES-OVINE PROLACTINS 16 pregnant, non-lactating, cross-bred beef cows in their last 30-105 days of gestation were divided into 2 groups and tested for the effects of intramammary infusion using the procedures of Examples 25-28 except that instead of a prostaglandin, each treatment infusion contained either 2 mg (Group 1) or 10 mg (Group 2) of ovine prolactin obtained from Sigma Chemical Co., St. Louis, Mo. (Lot No. 26F-0076) in 10 ml of an emulsion of 0.9% saline containing 0.5% Tween-20 in sterile sesame oil containing 5% Arlacel A (3:2 oil: saline). Results are in Tables 22-23.

TABLE 22

Effects of Intramammary Infusion of Ovine Prolactin (a Total of 10 Milligrams) on Quarter-Udders in Pregnant Beef Cattle (Group 1)

| | Wet Weight, g | Dry Weight, g | Dry Fat-Free Weight, g | DNA, mg |
|---|---|---|---|---|
| A. Treatment Mean | 895.3 | 262.7 | 137.8 | 2526 |
| B. Control Mean | 889.9 | 257.9 | 136.6 | 2566 |
| C. Mean Increase (A-B) | 5.4 | 4.8 | 1.2 | (40) |
| D. % Increase, (A-B)/B | .6 | 1.0 | .88 | (1.6) |
| E. Sig. Level of % Increase, $p<$ | 0.85 | 0.8 | 0.97 | — |

TABLE 23

Effects of Intramammary Infusion of Ovine Prolactin (Total dose of 50 milligrams) on Quarter-Udders in Pregnant Beef Cattle (Group 2)

| | Wet Weight, g | Dry Weight, g | Dry Fat-Free Weight, g | DNA, mg |
|---|---|---|---|---|
| A. Treatment Mean | 1487.1 | 343.4 | 189.2 | 3672 |
| B. Control Mean | 1308.5 | 349.0 | 184.5 | 3322 |
| C. Mean Increase (A-B) | 178.6 | (5.6) | 4.7 | 350 |
| D. % Increase, (A-B)/B | 13.6 | (1.6) | 2.5 | 10.5 |
| Sig. Level of % Increase, $p<$ | 0.09 | — | 0.7 | 0.27 |

J. Transforming Growth Factors-alpha

Alpha-type transforming growth factors have been purified as described by Samsoondar, J. et al. (1986) J. of Biological Chemistry 261: 14408-14413 and Korbin, M. et al. (1987) Endocrinology 121: 1412-1416. In order to obtain large quantities of alpha-type transforming growth factors, chemical synthesis and/or genetic engineering (e.g. recombinant DNA) methodologies are the preferred methods of synthesis.

This Example sets forth preferred methods for producing synthetic bovine transforming growth factor-alpha (TGF-α). This Example also describes the use of the synthetic TGF-α to enhance the growth of mammary parenchyma and its use to enhance the lactation of female mammals. The term "synthetic" as used herein means chemically and/or enzymatically (e.g. by recombinant DNA techniques) generated proteins essentially free of other proteins which they are naturally found associated with.

TGF-α interacts with the epidermal growth factor (EGF) receptor to stimulate a variety of biological activities, including the stimulation of DNA synthesis and cell growth. The sequence and synthesis of human TGF-α can be achieved as described by Reynolds, F. H. et al. (1981) Nature 292:295 and Tam, J. P. et al. (1986) Proc. Nat'l. Acad. Sci. USA 83:8082-8086. Human TGF-α is also commercially available as described in Example E, above. Across species, the amino acid sequence of TGF-α proteins appear to be highly conserved. To the extent that TGF-α's derived from different mammalian species or that molecular variations of such TGF-α proteins (e.g. allelic variants, deletion or amino acid substitutions therein), analogs thereof, or other compounds that function similarly in the mammary gland following intramammary infusion and achieve objectives of this invention in substantial measure, they are equivalents of such TGF-α's for purposes of this invention. It being further understood that such equivalent molecules can be made in accordance with the general methods described in this Example J.

Chemical Synthesis

Bovine TGF-α is a 50 amino acid polypeptide with three disulfide bonds. The primary amino acid sequence of bovine TGF-α is as follows (reading from the amino end to the carboxy end of said sequence):

$NH_2$-VAL-VAL-SER-HIS-PHE-ASN-ASP-CYS-PRO-ASP-SER-HIS-SER-GLN-PHE-CYS-PHE-HIS-GLY-THR-CYS-ARG-PHE-LEU-VAL-GLN-GLU-GLU-LYS-PRO-ALA-CYS-VAL-CYS-HIS-SER-GLY-TYR-VAL-GLY-ALA-ARG-CYS-GLU-HIS-ALA-ASP-LEU-LEU-ALA-COOH.

As used herein, the symbols representing amino acids (e.g. Ala for alanine) and nucleotide (G, T, C or A) are those conventionally employed. See Lehninger, A. L. (1976) Biochemistry, 2nd Ed., Worth Publishers, Inc. New York, N.Y., pp. 72-75, 315-322.

Synthesis of bovine TGF-α peptides having the above amino acid sequence can be accomplished by solid phase synthesis techniques on an ABI-430A automated solid-phase synthesizer (Applied Biosystems, Inc., Foster City, Calif.) essentially as described by Kent, S. and Clark-Lewis, I. in *Synthetic Peptides in Biology and Medicine*, Alitalo, K. and Valeri, A. (eds), Elsevier, Amsterdam (1986) pp. 29-56. Assembly was done on 0.44 mmole of BOC-Ala-Pam-resin, using BOC-protected amino acids having the following side-chain protection: Arg(Tos), Asp(OcHex), Cys(4-MeBzl), Glu(OcHex), His(BOM), Lys($Cl_2$Z), Ser(Bzl), Tyr(BrZ). Each position was double coupled using the preformed symmetrical anhydrides, except for Arg, Asn, His and Gln residues, which were double coupled using the HOBTesters. Dimethysufide (0.1%) was added to the TFA during removal of the BOC-protecting groups to avoid S-tert-butylation of the Cys sidechain. The completed peptide resin was subjected to low-high HF cleavage essentially as described by Tam, S. P. et al. (1983) J. Am. Chem. Soc. 105: 6442–6445 and Tam, J. P. et al. (1986) Proc. Nat'l. Acad. Sci., U.S.A. 83: 8082–8086, the resulting precipitate washed with cold anhydrous diethyl ether/mercaptoethanol 99/1 (v/v), and the peptide extracted into 8M urea/0.1M Tris/0.2M DTT (pH8). The peptide solution was dialyzed stepwise against 8M, 4M then 2M urea, all in 0.1M DTT, 0.1M Tris-HCl (pH 8.1.) The DTT was removed by further dialysis (2×) with 2M urea in 0.1M Tris-HCl (pH 8.1). After refolding, peptide buffer was exchanged to 1M acetic acid by a series of dialysis against each of the following solutions: 0.1M Tris buffer (pH 8.1), water and 1M acetic acid. The resultant peptide solution was then filtered (0.45 um) and then isolated by single HPLC purification on Waters RPC-18 Delta-Pak (Waters Assoc., Millford, Mass.). The integrity of the peptide and primary amino acid sequence was confirmed by demonstration of a distinct mass spectrum peak at 5547 (M+H) and by conventional peptide mapping using chymotrypsin, amino acid analysis and gas-phase-sequencing of the first 33 amino acid residues, respectively. The three disulfide bond pairings in the folded, synthetic bovine TGF-α peptides were confirmed by a conventional peptide mapping procedure using thermolysin.

Genetic Engineering

Recombinant production of bovine TGF-α in such Gram-negative microorganisms as E. coli is accomplished by conventional genetic engineering methodologies (see Maniatis et al., 1982, Molecular Cloning: A Laboratory Manual, Cold Spring Harbor Laboratory, Cold Spring Harbor, N.Y.).

As used, herein, the term "gene" refers to DNA sequences which provide for production of protein(s) encoded therein in selected host cells. The term "synthetic" is understood to mean a chemically and/or enzymatically generated nucleic acid sequence or molecule free from naturally occurring, intervening or contiguous sequences. Also embraced in the term "synthetic" are chemically and/or enzymatically generated molecules or sequences which are combined with nucleic acid sequences or molecules with which they are not naturally found associated or combined. Examples of synthetic genes, molecules or sequences include, but are not limited to, nucleic acid sequences enzymatically or chemically released from a larger (e.g. naturally occurring) molecule and genomic DNA which has been modified by nucleic acid addition, deletion and/or rearrangement. The term "genome" or "genomic" as used herein means the total DNA (e.g. chromosomal and extrachromosomal) contained within a given cell.

For direct or intact synthesis of TGF-α proteins, a synthetic gene is constructed which contains the following components sequentially aligned in a 5' to 3' orientation: a promoter, a ribosome binding site, a translation start/signal codon (e.g. AUG) contiguous with a DNA sequence encoding a bovine TGF-α peptide and a translation stop codon.

In constructing a synthetic gene or genes which encode bovine TGF-α, any promoter capable of causing transcription in Gram-negative bacteria of such a gene or genes can be employed. Examples of such promoters are well known and available to those skilled in the art and include, without limitation, bacterial, viral and plasmid gene promoters (See Rosenberg and Court, 1979 Ann. Rev. of Genet. 13: 319–353). DNA molecules containing such promoter sequences can be isolated either by cloning the desired regions or, more conveniently, by chemically synthesizing them.

In one embodiment, synthetic genes able to provide for production of TGF-α in such Gram-negative host cells as E. coli employ the E. coli recA promoter, the sequence of which has been published (see Sancar & Rupp, 1979, Proc. Nat'l. Acad. Sci., U.S.A. 76: 3144–3148; Sancar, A. et al., 1989, Proc. Nat'l. Acad. Sci., U.S.A. 77: 2611–2615).

In a preferred embodiment, a hybrid promoter (Tac) derived from the E. coli trp and lac-UV5 promoter sequences is employed. The Tac promoter has the following DNA sequence reading from the 5' end to the 3' end:

5'-TTCTGAAATGAGCTGTTGACAATTAAT-CATCGGCTCGTA
TAATGTGTGGAATTGTGAGC-GGATAACAATTTCACACA-3'

This sequence can be synthesized by conventional means, and inserted into a selected expression vector by such conventional means as blunt-end ligation. In one preferred embodiment, the Tac promoter sequence is synthesized so as to contain different restriction endonuclease sites at either end. These restriction sites facilitate site-specific and orientation-specific insertion in cloning and expression vectors.

In procaryotic systems, a ribosome binding site such as a Shine-Dalgarno Sequence (Shine & Dalgarno, 1974, Proc. Nat'l. Acad. Sci., U.S.A. 71: 1342–1346) has been demonstrated to be required for efficient translation of messenger RNA molecules. The nucleotide sequences of more than 120 ribosome binding sites of E. coli mRNAs are now known (see Scherer et. al., 1980, Nucleic Acids Res. 8: 3895–3907; Gold et al., 1981, Ann. Rev. Microbiol. 35: 365–403). A preferred synthetic gene encoding bovine TGF-α employed herein, contains a ribosome binding site derived from the gene 10 of bacteriophage T7, described more fully in European Patent Application Publication No. 0241,446, published on Oct. 14, 1987.

The primary amino acid sequence of bovine TGF-α is set forth above (see Chemical Synthesis section). From the primary amino acid sequence, a plurality of DNA coding sequences can be constructed based upon the degeneracy of the genetic code. Selection of the specific amino acid codons to be employed in generating a bovine TGF-α coding sequence is generally guided by such factors as determining a sequence which will optimize transcription, translation and, ultimately, the amount of protein produced. Typically, host preferred codons are chosen. Examples of E. coli preferred codons are described by Fiers et al., (1976) Nature 260: 500. Alternatively, a bovine TGF-α coding sequence can be isolated as a genomic fragment from which introns are removed.

In performing direct or intact synthesis of TGF-α, a DNA sequence encoding a bovine TGF-α protein can be inserted into commerically available expression vectors (Stratagene, LaJolla, Calif.; Promega, Madison, Wis.; Pharmacia, Piscataway, N.J.) or one available to one of ordinary skill in the art. The resultant TGF-α proteins, however, typically contain an additional NH₂-terminal methionine owing to the requisite translation start/signal methionine codon.

In one embodiment, the gene construct used for direct TGF-α synthesis contains an additional alanine (ala) codon at the NH₂-terminus of the DNA sequence encoding the native bovine TGF-α protein. The bovine TGF-α protein produced by such means contains an alanine amino acid at its NH₂-terminus in place of the additional NH₂-terminal methionine.

Alternatively, TGF-α can be produced as a fusion protein. A fusion protein typically contains an endogenous host protein on fragment thereof contiguous with the amino terminus of the desired protein (e.g. TGF-α). When such a gene construct is used, the start/signal methionine codon is contiguous with the first amino acid of the endogenous protein or protein fragment. Fusion constructs result in production of a chimeric protein, a protein that is part host and part non-host (e.g. TGF-α). The desired non-host protein (e.g. TGF-α) must then be separated, by chemical or enzymatic cleavage, from the host protein fragment. Synthesis of both intact and fusion proteins containing bovine TGF-α can be performed as essentially described in Maniatis et al., supra.

In the present example, a synthetic DNA sequence encoding a bovine TGF-α peptide using *E. coli* preferred codons is constructed and assembled in accordance with the methods described by Scarpulla R. C. et al. (1982) J. Biological Chem. 257: 9226; and Adams, S. & Galluppi, G. R. (1986) Medicinal Res. Reviews 6: 135. In one embodiment, a synthetic DNA coding sequence comprising a TrpE-TGF-α fusion protein is constructed. The synthetic sequence thus encodes the following sequence (reading from the amino end to the carboxy end of said sequence) of amino acids contiguous with the amino terminus of the TGF-α protein: MET-GLN-THR-GLN-LYS-PRO-THR-PRO-SER-MET-TGF-α. The methionine immediately preceding the first amino acid of the mature or native TGF-α protein serves as the site for cyanogen bromide cleavage of the fusion protein to effect the release of intact TGF-α eins. Bovine TGF-α contains no internal methionines.

The synthetic sequence encoding a TrpE-TGF-α fusion protein is then inserted into a pBR327 *E. coli* plasmid which has been modified to contain the before described Tac promoter and ribosome binding site from the gene 10 of bacteriophage T7, so that the Tac promoter and ribosome binding site both control the expression of the TrpE-TGF-α fusion protein. *E. coli* host cells, such as *E. coli* strain W3110, deposited with the ATCC in accordance with the Budapest Treaty and having ATCC accession number 27325, are then transformed with the modified pBR327 plasmids essentially as described in Maniatis et al., supra. The growth media for the *E. coli* and conditions for selection of bacterial cells carrying the plasmids are essentially as described by Maniatis et al., supra.

Induction of transcription (e.g. expression of the TrpE-TGF-α gene) from the Tac promoter is conducted briefly as follows. Overnight cultures of *E. coli* host cells carrying expression plasmids are inoculated into a 15 liter LSL Biolafitte fermentor (LSL Biolafitte, France) containing M9 minimal media supplemented with 10 grams per liter glucose and 20 grams per liter casamino acids. Thiamine is also added to a final concentration of 2.5 μg/ml. The cells are grown to a density of 12.5 optical density units at 550 nm (Gilford Stasar II spectrometer) and induced by adding isopropyl beta-D-thiogalactopyranoside (IPTG) to the fermentor to a final concentration of 0.00238 grams per liter. Glucose is depleted from the medium at an optical density (O.D. 550) of 25.0 and lactose is added to the fermentor to a final concentration of 10 grams per liter to further induce the culture. Induction is continued for several hours at 37° C. and the culture is harvested by conventional concentration and centrifugation. The cell paste is stored at −80° C.

Frozen cells (400 grams wet weight) from the equivalent of a 10-liter fermentation are thawed and suspended in 8 liters of chilled water from a Waters Milli-Q System (Waters Assoc., Millfor, Mass.). The cells are disrupted by passing the suspension through a Manton-Gaulin Homogenizer Model 15-8TA(APV Gaulin Inc., Everett, Mass.)×3 at 9000 psi. Inclusion bodies are collected at 13000×g for 30 minutes. Pellets are resuspended in chilled water and centrifuged as before for collection.

Inclusion bodies (20–30 grams wet weight) are solubilized in 7.5M urea, 20 mM tris pH 8.5, 10 mM EDTA, 100 uM PMSF(1 liter). Sodium sulfite is added (20 grams) and the preparation is allowed to stir for 20 minutes at room temperature before the addition of sodium dithionite (10 grams). The reaction is allowed to proceed overnight. The procedure is repeated the next morning with 2 hours of stirring before employing diafiltration versus water using a Pharmacia (Piscataway, N.J.) 150 mm Omega membrane (3000 MW exclusion) to reduce the volume to 100 ml.

In cases where the inclusion bodies contain less than an estimated 50–60% TGFα by SDS-PAGE analysis (described below), the sulphonyl protein is purified using a Q-Sepharose Fast Flow (Pharmacia, Piscataway, N.J.) column (5×15 cm) equilibrated with 3.75M urea, 20 mM tris pH 8.5, 10 mM EDTA, 100 uM PMSF. The sulphonyl TrpE-TGF-α is eluted with a 5 column volume gradient of equilibration buffer and one molar sodium chloride in equilibration buffer. The flow rate is maintained at 20 ml/minute with the effluent monitored for absorbance at 280 nanometers. Sulphonyl TrpE-TGF-α peak fractions are determined by SDS-PAGE analysis.

The SDS-PAGE analysis referred to above is conducted on 20% polyacrylamide gels essentially as described by Hames, B. D. in Gel Electrophoresis of Proteins (1981), Hames, B. D. and Rickwood eds., IRL Press, Oxford, England, Chapter 1, pp. 1–91, or with Pharmacia (Piscataway, N.J.) Phast gels with an 8–25% polyacrylamide gradient in accordance with manufacturers instructions.

In cases where the inclusion bodies represent 60% TrpE-TGF-α or greater, the sulphonate preparation is carried through sulphitolysis/refold without further purification. The buffer is exchanged to 20 mM 1,3-diaminopropane-HCl pH 10 by diafiltration (as previously described) and the refold initiated by the addition of solid cysteine to a concentration of 0.15 mM with stirring at 4° C. Conversion of reduced TrpE-TGF-α and folding intermediates to the correctly folded form is determined by analytical RP-HPLC using a Brownlee (Brownlee Labs, Santo Clara, Calif.) C-8 column (0.21×3 cm) in conjunction with either a Waters 840 System (Waters Assoc., Millford, Mass.) or an Applied Biosystems Model 130A Microbore HPLC system (Applied Biosystems, Inc., Foster City, Calif.) in accordance with manufacturers instructions.

The refold preparation is set up for the cyanogen bromide reaction (e.g. cleavage of the fusion protein and release of intact bovine TGF-α proteins) by exchanging the buffer for 0.1N HCl (500 ml) by diafiltration and centrifugation at 13000×g for 30 minutes to remove the resulting precipitate. Solid cyanogen bromide is added directly (1.2 grams) followed by stirring for 24 hours at room temperature. The cleavage reaction is followed by RP-HPLC using aliquots of the solution that have been microdialyzed vs. water. Following completion of the reaction, the volume is reduced by diafiltration and the solution dialyzed against water. The preparation is frozen in a dry ice-acetone bath and placed on a Virtus Freezemobile Model 12 lyophilizer (Virtus, Gardner, N.Y.) for 48 hours to obtain the TrpE-TGF-α as a dry power. The integrity and chemical structure of the bovine TGF-α proteins so produced is confirmed by conventional N-terminal amino acid sequence analysis, amino acid composition and mass spectroscopy.

Effect of bovine TGF-α on Mammary Parenchyma

The ability of synthetic bovine TGF-α to stimulate and enhance the growth of mammary parenchyma can be evaluated by its ability to stimulate bovine mammary epithelial cell proliferation in vitro as follows. Bovine mammary cells are isolated and cultured in a three-dimensional collagen matrix according to the methods of McGrath, M. F. (1987) J. Dairy Sci. 70: 1967–1980. Briefly, mammary tissue is obtained from non-lactating cows which have completed approximately 150 days of gestation. Tissue is chopped to a fine mince and approximately 10 grams placed in a fluted 500 ml Erlenmeyer flask. 75 ml of wash medium (Medium 199, Grand Island Biological Corporation (GIBCO), Grand Island, N.Y.; antibiotic/antimycotic, GIBCO; and gentamycin sulfate, (GIBCO) containing 0.15% collagenase (CLSII) (Worthington Corp., Bedford, Mass.), 0.1% hyaluronidase (Type I) (Sigma Chemical Co., St. Louis, Mo). and 6.6% fetal bovine serum (FBS) (GIBCO) is added to each flask. The dissociation mixture is swirled on a gyratory water bath at 100 rpm at 32° C. for 3 to 4 hours. Dispersed mammary fragments are collected by centrifiguration. Mammary fragments are pooled and resuspended in 25 ml of wash medium containing 10% FBS plus 0.01% DNase (deoxyribonuclease I), (Sigma Chemical Co., St. Louis, Mo.) and filtered through 150 um Nitex cloth (Tetko Co., Elmsford, N.Y.) to remove non-dispersed material. To separate epithelial from non-epithelial components, fragments are resuspended in 1 ml of 0.02% DNase and layered on a preformed density gradient (28 ml, 42% Peroll) (Pharmacia Fine Chemicals, Piscataway, N.Y.). Fragments are separated by centrifugation for 10 minutes at 800×g. Epithelial components are collected from the 1.065 to 1.07 g/cc density region of the gradient.

For culture, freshly dissociated or cryopreserved cells in a minimum volume of Medium 199 are added to cold, neutralized collagen at a final concentration of 4 to 6×10$^5$ cells/ml. The collagen-cell suspension (0.5 ml) is overlaid on 0.3 ml pregelled collagen in each well of a 24 multiwell plate (Costar, Cambridge, Mass.) and allowed to gel at room temperature. Cultures are then fed with 0.5 ml of a 1:1 mixture of DME:Ham's F-12 medium (GIBCO) containing 3% FBS, antibiotics, and 1 ng/ml, 5 ng/ml, 10 ng/ml, 25 ng/ml or 100 ng/ml synthetic TGF-α. Control cultures receive no TGF-α. After 12 days of incubation, cultures are terminated and bioactivity estimated by measuring increase in total DNA in each well. A six-fold increase in cell proliferation is observed when synthetic bovine TGF-α is present from about 1 ng/ml to about 100 ng/ml.

The significant increase in mammary epithelial cell proliferation following administration of bovine TGF-α indicates a strong ability of TGF-α to enhance the growth of mammary parenchyma.

Effect of Intramammary Infusion of Bovine TGF-α on Subsequent Milk Production

Seven pregnant Holstein heifers are given ten daily infusions of bovine TGF-α beginning fifty days prior to expected calving. The lyophilized TGF-α is suspended in 10 ml of an excipient (physiologic saline) and administered at a dose of 250 μg per quarter udder per infusion as previously described in Examples 23-24. Control animals and control halves (both quarter udders on the opposite side of the treated quarter udders) are not infused. Milk production is monitored through 23 weeks of lactation milk production.

TABLE 24

Effect of Intramammary Infusion of Bovine TGF-α on Quarter-Udders in Pregnant Holstein Heifers

| Average Milk Production kg/day | | | |
|---|---|---|---|
| Treated (A) | Control (B) | % Increase (A-B)/B | Sig. Level of Increase (p<) |
| 34.0 | 30.6 | 11.1 | 0.11 |
| 35.6* | 31.3* | 13.7* | 0.11 |

*The post-peak milk response to bovine TGF-α infusion for weeks 7-20.

As shown in Table 24, above, heifer quarter-udders infused with bovine TGF-α produce substantially more milk than untreated heifer quarter-udders.

While the biological mechanisms of this invention are not fully understood, it is apparent that it can be used to provide, in accordance with conventionally recognized criteria, increases in mammary parenchyma and corresponding milk production capacity of treated animals that will persist through the animal's next lactation period, and in many cases through multiple subsequent lactations.

We claim:

1. A method for enhancing the lactation of a mammal comprising administering to the mammal by intramammary infusion during gestation or between about the onset of puberty and the mammal's first gestation a lactation enhancing amount of transforming growth factor-alpha (TGF-α).

2. The method of claim 1 wherein the transforming growth factor-alpha is administered during gestation.

3. The method of claim 1 or 2 wherein the TGF-α is a synthetic protein.

4. The method of claim 1 or 2 wherein the lactation enhancing amount of transforming growth factor-alpha is between about 25 micrograms and about 10 milligrams.

5. A method for enhancing the growth of mammary parenchyma in a physiologically normal mammal wherein a mammary parenchyma growth-enhancing amount of transforming growth factor-alpha is administered to the mammal by intramammary infusion during gestation or between about the onset of puberty and the mammal's first gestation.

6. The method of claim 5 wherein the transforming growth factor-alpha is bovine transforming growth factor-alpha.

7. The method of claim 6 wherein the bovine transforming growth factor-alpha is a synthetic protein.

8. The method of claim 5 wherein the growth-enhancing amount is between about 25 micrograms to about 10 milligrams.

9. The method of claim 5 wherein the TGF-$\alpha$ is administered in a physiologically acceptable liquid vehicle.

10. The method of claim 9 wherein said physiologically acceptable vehicle is mineral oil, vegetable oil, saline solution or mixtures thereof.

11. The method of claim 10 wherein said vegetable oil is peanut oil or sesame oil.

12. The method of claim 9 wherein said TGF-$\alpha$ is administered in an amount of from about 2.5 micrograms to 250 micrograms per mammary gland per infusion.

13. The method of claim 12 wherein a total of 12.5 micrograms to 1.25 mg per gland is infused over a period of from 1 to about 10 days.

14. The method of claim 13 wherein said mammal has a four gland undder and the total amount of TGF-$\alpha$ administered over the period of treatment is from about 50 micrograms to 5 mg.

15. The method of claim 12 wherein said mammal is a cow.

16. The method of claim 15 wherein said TGF-$\alpha$ is bovine TGF-$\alpha$.

17. The method of claim 13 wherein said mammal has a two gland udder and the total amount of TGF-$\alpha$ administered over the period of treatment is from about 25 micrograms to 2.5 mg.

18. The method of claim 17 wherein said mammal is a sheep or goat.

19. The method of claim 9 wherein the TGF-$\alpha$ is infused in from 1 to about 10 ml of liquid vehicle.

20. The method of claim 9 wherein said vehicle is substantially liquid at the body temperature of said mammal.

21. The method of claim 9 wherein said TGF-$\alpha$ is substantially soluble in said liquid vehicle.

22. The method of claim 9 wherein the mammal is a swine.

23. The method of claim 9 wherein said physiologically acceptable vehicle is saline solution.

* * * * *